United States Patent
Kreidler et al.

(10) Patent No.: US 8,404,902 B2
(45) Date of Patent: Mar. 26, 2013

(54) METHOD FOR SEPARATING 1-BUTENE FROM $C_4$-CONTAINING HYDROCARBON STREAMS BY HYDROFORMYLATION

(75) Inventors: Burkard Kreidler, Recklinghausen (DE); Klaus-Diether Wiese, Haltern am See (DE); Dieter Hess, Marl (DE); Detlef Selent, Rostock (DE); Armin Boerner, Rostock (DE)

(73) Assignee: Evonik Oxeno GmbH, Marl (DE)

( * ) Notice: Subject to any disclaimer, the term of this patent is extended or adjusted under 35 U.S.C. 154(b) by 160 days.

(21) Appl. No.: 12/992,032

(22) PCT Filed: Apr. 28, 2009

(86) PCT No.: PCT/EP2009/055121
§ 371 (c)(1), (2), (4) Date: Nov. 10, 2010

(87) PCT Pub. No.: WO2009/146984
PCT Pub. Date: Dec. 10, 2009

(65) Prior Publication Data
US 2011/0071321 A1    Mar. 24, 2011

(30) Foreign Application Priority Data
Jun. 3, 2008 (DE) .......... 10 2008 002 188

(51) Int. Cl.
*C07C 45/50* (2006.01)
*C07C 29/16* (2006.01)

(52) U.S. Cl. .......... 568/450; 568/454; 568/880

(58) Field of Classification Search .......... 568/450, 568/454, 880
See application file for complete search history.

(56) References Cited

U.S. PATENT DOCUMENTS

| | | | |
|---|---|---|---|
| 4,287,370 A | 9/1981 | Harris et al. | |
| 4,668,651 A | 5/1987 | Billig et al. | |
| 6,331,657 B1 | 12/2001 | Kaizik et al. | |
| 6,403,837 B1 | 6/2002 | Hess et al. | |
| 6,570,033 B2 | 5/2003 | Rottger et al. | |
| 7,009,068 B2 | 3/2006 | Schmutzler et al. | |
| 7,161,020 B2 | 1/2007 | Selent et al. | |
| 7,361,786 B2 | 4/2008 | Boerner et al. | |
| 7,495,133 B2 | 2/2009 | Borgmann et al. | |
| 7,589,215 B2 | 9/2009 | Boerner et al. | |
| 2002/0111487 A1 | 8/2002 | Roettger et al. | |
| 2003/0144559 A1 | 7/2003 | Hess et al. | |
| 2003/0195368 A1 | 10/2003 | Rottger et al. | |
| 2004/0138508 A1 | 7/2004 | Tinge et al. | |
| 2005/0209455 A1 | 9/2005 | Boerner et al. | |
| 2007/0106102 A1* | 5/2007 | Caers et al. | 585/16 |
| 2010/0036143 A1 | 2/2010 | Selent et al. | |

FOREIGN PATENT DOCUMENTS

| | | |
|---|---|---|
| DE | 10 2006 058682 | 6/2008 |
| EP | 0 016 286 | 10/1980 |
| EP | 1 312 598 | 5/2003 |
| WO | 2008 124468 | 10/2008 |

OTHER PUBLICATIONS

International Search Report issued Nov. 2, 2009 in PCT/EP09/055121 filed Apr. 28, 2009.
European Search Report issued Jan. 31, 2013, in European Patent Application No. 12195793.0.

* cited by examiner

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a method for separating 1-butene from $C_4$-containing hydrocarbon mixtures, comprising isobutene and 1-butene, by hydroformylation, wherein the catalytic system used is made of one of the transition metals of the group 8 to 10, preferably rhodium, and a bisphosphite ligand of the formula (I), where X is a divalent substituted or unsubstituted bisalkylene or bisarylene group having one or more heteroatom(s), Y is a divalent substituted or unsubstituted bisarylene or bisalkylene group having one or more heteroatom(s), Z is oxygen or $NR^9$, and $R^1$, $R^2$, $R^3$, $R^4$ are identical or different, substituted or unsubstituted, linked, unlinked or condensed aryl or heteroaryl groups, and $R^9$ is hydrogen or a substituted or unsubstituted alkyl or aryl group having one or more heteroatom(s), wherein the bisphosphite ligand of the formula (I) is used in an excess of a molar ratio of 100:1 to 1:1 to the transition metal, and that with a 1-butene conversion of more than 95% less than 5% of the present isobutene is reacted method for separating 1-butene from $c_4$-containing hydrocarbon streams by hydroformylation.

19 Claims, No Drawings

METHOD FOR SEPARATING 1-BUTENE FROM C₄-CONTAINING HYDROCARBON STREAMS BY HYDROFORMYLATION

The present invention relates to the selective hydroformylation of 1-butene to valeraldehyde from $C_4$-containing hydrocarbon streams which comprise both 1-butene and isobutene.

Isobutene is frequently present in industrial streams together with saturated and unsaturated $C_4$ hydrocarbons. Owing to the small boiling point difference and/or the very low separation factor between isobutene and 1-butene, isobutene cannot be removed economically from these mixtures by distillation. Isobutene is therefore typically obtained from industrial hydrocarbon mixtures by converting isobutene to a derivative which can be removed easily from the remaining hydrocarbon mixture, and by dissociating the isolated derivative to isobutene and derivatizing agent.

Isobutene is the starting material for the preparation of a multitude of products, for example for the preparation of butyl rubber, polyisobutylene, isobutene oligomers, branched $C_5$ aldehydes, $C_5$ carboxylic acids, $C_5$ alcohols and $C_5$ olefins. In addition, it is used as an alkylating agent, especially for the synthesis of tert-butyl aromatics, and as an intermediate for the production of peroxides. In addition, isobutene can be used as a precursor for the preparation of methacrylic acid and esters thereof.

Typically, isobutene is removed from $C_4$ cuts, for example the $C_4$ fraction of a steamcracker, as follows:

After removal of the majority of the polyunsaturated hydrocarbons, principally butadiene, by extraction/extractive distillation or selective hydrogenation (SHP) to linear butenes, the remaining mixture (raffinate I or selectively hydrogenated crack-$C_4$) is reacted with alcohol or water. Isobutene forms methyl tert-butyl ether (MTBE) in the case of use of methanol, ethyl tert-butyl ether (ETBE) in the case of ethanol, and tert-butanol (TBA) in the case of use of water. On completion of derivatization and removal, all three products can be dissociated to isobutene in a reversal of their formation. For the isolation of isobutene, as well as various separating operations, at least two reaction stages are accordingly required.

Alternatively, isobutene can be removed from a $C_4$ hydrocarbon stream which typically contains less than 1% by mass of butadiene ($C_4$ stream from fluid catalytic cracking processes, raffinate I or selectively hydrogenated crack-$C_4$), in the following manner:

The starting mixture is hydrogenated and isomerized, i.e. butadiene (still) present is selectively hydrogenated down to a residual content of below 5 ppm by mass, and 1-butene is simultaneously isomerized to 2-butenes. The equilibrium position between 1-butene and the isomeric 2-butenes is, for example at 80° C., at a ratio of 1:17.

When the isomerization is performed in a reactive distillation, a virtually 1-butene-free top product can be removed, from which pure isobutene can be worked up further. The bottom product obtained is an isobutene-free mixture of 2-butenes. However, a disadvantage is that the isobutene has a lower purity than the product prepared by the method of derivatization. Moreover, 1-butene is converted to the less reactive and also economically less attractive 2-butenes.

A further alternative consists in exploiting the higher reactivity of 1-butene compared to isobutene in the hydroformylation, in order to selectively remove 1-butene from the mixture by hydroformylation. However, the reactivity differences of 1-butene and isobutene are generally too low to achieve selectivities of commercial interest.

EP 0 016 286 presents a process with which 1-butene can be converted selectively to valeraldehyde in the presence of isobutene. In the process described there, however, an at least 100-fold excess of phosphine ligand is required in order to achieve the desired selectivities, which again makes the process unattractive.

International application WO 2005/028404 makes use of the same process in its examples. This also claims, without specifying experimental details, achievement of not more than 5% isobutene conversion at 65% 1-butene conversion with the ligands A described there.

However, a 65% 1-butene conversion can in no way be considered to be sufficient to satisfactorily solve the technical problem of separating 1-butene and isobutene. A technical solution should lower the 1-butene content well below the thermodynamic equilibrium between 1-butene and the isomeric 2-butene, in order subsequently to be able to distil off isobutene freed of 1-butene. A minimum requirement can be considered to be a 1-butene conversion of 95% with not more than 5% isobutene conversion. Preference is given to a 1-butene conversion of at least 99% at an isobutene conversion of not more than 5%.

The technical problem was therefore to develop a process with which 1-butene can be hydroformylated selectively from a $C_4$-containing hydrocarbon mixture which comprises isobutene and 1-butene and may comprise 2-butenes, without isobutene also reacting in the same way. Ideally, 2-butenes which are optionally present are hydroformylated or isomerized to a minimum degree, such that the end concentration of 1-butene is considerably below the concentration of 1-butene in the thermodynamic equilibrium between 1-butene and 2-butenes. A minimum requirement can be considered to be a 1-butene conversion of 95% at not more than 5% isobutene conversion. 1-Butene shall be hydroformylated with an n/iso selectivity of at least 97% at the terminal carbon atom to give n-valeraldehyde. The process shall need considerably lower ligand excesses than EP 0 016 286. This problem has been solved by a process for removing 1-butene from $C_4$-containing hydrocarbon mixtures comprising isobutene and 1-butene by hydroformylation, the catalyst system used consisting of one or the transition metals of groups 8 to 10, preferably rhodium, and a bisphosphite ligand of the following formula I

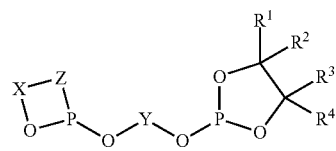

where X=divalent substituted or unsubstituted bisalkylene or bisarylene radical which contains one or more heteroatom(s), Y=divalent substituted or unsubstituted bisarylene or bisalkylene radical which contains one or more heteroatom(s), Z=oxygen or $NR^9$, and $R^1$, $R^2$, $R^3$, $R^4$ are identical or different, substituted or unsubstituted, connected, unconnected or fused aryl or heteroaryl radicals, and $R^9$=hydrogen or substituted or unsubstituted alkyl or aryl radical which contains one or more heteroatom(s), the bisphosphite ligand of the above-specified formula I being used in an excess of a molar ratio of 100:1 to 1:1 relative to the transition metal, and less than 5% of the isobutene present being converted at a 1-butene conversion of more than 95%.

It has now been found that, from a $C_4$-containing hydrocarbon mixture comprising isobutene and 1-butene, the 1-butene can be converted by hydroformylation at temperatures below 120° C., preferably below 100° C., to $C_5$ aldehydes from the hydrocarbon mixture to an extent of more than 99% by weight, the conversion of the isobutene present being less than 5% by weight, when a catalyst system consisting of rhodium and a bisphosphite, described in DE 10 2006 058682, is used and the reaction temperature is below 100° C. Subsequently, the hydroformylation mixture is preferably separated into a $C_5$ aldehyde fraction, pure isobutene, into a catalyst fraction and into a fraction comprising the remaining hydrocarbons, the $C_5$ aldehyde fraction consisting of valeraldehyde with an n/iso selectivity of more than 97%.

The process according to the invention has the following advantages: with only one chemical reaction and a distillative workup, two sought-after intermediates are obtained from a $C_4$ hydrocarbon mixture comprising isobutene and 1-butene, specifically isobutene and the $C_5$ aldehyde mixture with a high proportion of valeraldehyde. In addition, any hydrocarbon mixture comprising the isomeric 2-butenes obtained can be utilized for further reactions, for example for the preparation of oligomers or $C_5$ aldehydes.

Feedstocks for the process according to the invention are, for example, light petroleum fractions from refineries, $C_4$ fractions from cracking plants (for example steamcrackers, hydrocrackers, catcrackers), mixtures from Fischer-Tropsch syntheses, mixtures formed by metathesis of olefins, mixtures which are obtained by dehydrogenating saturated hydrocarbons, and mixtures which arise from methanol (or other oxygenates) to olefin (MTO) processes. These techniques are described in the technical literature (H. J. Arpe, Industrielle Organische Chemie [Industrial Organic Chemistry], Wiley-VCH, 6th Edition, 2007, pages 9-12, 23, 36, 93-97, 120).

Preferred feedstocks among those mentioned above are $C_4$ fractions from steamcrackers, which are operated primarily for production of ethene and propene and in which the raw materials used are, for example, refinery gases, naphtha, gas oil, LPG (liquefied petroleum gas) and NGL (natural gas liquid), $C_4$ fractions from catcrackers or products from butane dehydrogenation plants. According to the process, the $C_4$ cuts obtained as by-products contain different proportions of 1,3-butadiene, 1-butene, Z-2-butene, E-2-butene, isobutene, n-butane and isobutane.

For the process according to the invention, it is advantageous to remove polyunsaturated hydrocarbons, such as 1,3-butadiene, from the feed mixture. This can be done by known processes, for example by extraction, extractive distillation or complex formation (cf. H. J. Arpe, Industrielle Organische Chemie, Wiley-VCH, 6th Edition, 2007, pages 118-119).

An alternative to the removal of the polyunsaturated hydrocarbons is a selective chemical conversion. For example, 1,3-butadiene can be hydrogenated selectively to linear butenes, as described, for example, in EP 0 523 482. The 1,3-butadiene can also be removed at least partially by selective conversions of the 1,3-butadiene, for example dimerization to cyclooctadiene, trimerization to cyclododecatriene, polymerization or telomerization reactions. When a crack-$C_4$ cut has been used as the raw material, what remains in all cases is a hydrocarbon mixture (e.g. raffinate I or hydrogenated crack-$C_4$ ($HCC_4$)), which comprises principally the saturated hydrocarbons, n-butane and isobutane, and the olefins, isobutene, 1-butene and 2-butenes.

Typical compositions of $C_4$ cuts from which the majority of the polyunsaturated hydrocarbons have been removed and which can be used in the process according to the invention are listed in Table 1 below.

TABLE 1

| | Steamcracker | | Steamcracker | | Catcracker | |
| --- | --- | --- | --- | --- | --- | --- |
| Component | $HCC_4$ | $HCC_4$/SHP | Raff. I | Raff. I/SHP | $CC_4$ | $CC_4$/SHP |
| isobutane [% by mass] | 1-4.5 | 1-4.5 | 1.5-8 | 1.5-8 | 37 | 37 |
| n-butane [% by mass] | 5-8 | 5-8 | 6-15 | 6-15 | 13 | 13 |
| E-2-butene [% by mass] | 18-21 | 18-21 | 7-10 | 7-10 | 12 | 12 |
| 1-butene [% by mass] | 35-45 | 35-45 | 15-35 | 15-35 | 12 | 12 |
| isobutene [% by mass] | 22-28 | 22-28 | 33-50 | 33-50 | 15 | 15 |
| Z-2-butene [% by mass] | 5-9 | 5-9 | 4-8 | 4-8 | 11 | 11 |
| 1,3-butadiene [ppm by mass] | 500-8000 | 0-50 | 50-8000 | 0-50 | <10000 | 0-50 |

Explanation $HCC_4$: typical of a $C_4$ mixture which is obtained from the crack-$C_4$ of a steamcracker (high severity) after the hydrogenation of the 1,3-butadiene without additional moderation of the catalyst.

$HCC_4$/SHP: $HCC_4$ composition in which residues of 1,3-butadiene have been reduced further in a SHP.

Raff. I (raffinate I): typical of a $C_4$ mixture which is obtained from the crack-$C_4$ of a steamcracker (high severity) after the removal of the 1,3-butadiene, for example by an NMP extractive rectification.

Raff. I/SHP: Raff. I composition in which residues of 1,3-butadiene have been reduced further in an SHP.

$CC_4$: typical composition of a crack-$C_4$ which is obtained from a catcracker.

$CC_4$/SHP: $CC_4$ composition in which residues of 1,3-butadiene have been reduced further in an SHP.

The hydroformylation of the feed hydrocarbon mixture comprising isobutene and 1-butene is effected under conditions under which the 1-butene present in the feed mixture is converted to an extent of more than 95%, and the isobutene present in the feed mixture to an extent of less than 5%. Preferably, the 1-butene present in the feed mixture is converted to an extent of more than 99% and the isobutene present in the feed mixture to an extent of less than 5%. More preferably, the 1-butene is hydroformylated with an n/iso selectivity of more than 97%.

For the selective hydroformylation, preference is given to using catalyst systems consisting of rhodium and bisphosphites of the general formula I:

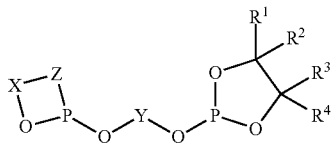

where
X=divalent substituted or unsubstituted bisalkylene or bisarylene radical which contains one or more heteroatom(s),
Y=divalent substituted or unsubstituted bisarylene or bisalkylene radical which contains one or more heteroatom(s),
Z=oxygen or $NR^9$,
$R^1$, $R^2$, $R^3$, $R^4$ are identical or different, substituted or unsubstituted, connected, unconnected, fused or unfused aryl or heteroaryl radicals,
and $R^9$=hydrogen or substituted or unsubstituted alkyl or aryl radical which contains one or more heteroatom(s). The $R^1$, $R^2$, $R^3$, $R^4$, $R^9$, X or Y radicals may be substituted, for example, by at least one radical selected from aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms, F, Cl, Br, I, $-CF_3$, $-(CH_2)_i(CF_2)_jCF_3$ where i=0-9 and j=0-9, $-SiR^{21}_3$, $-Si(OR^2)_3$, $-SiR^{21}(OR^{21})_2$, $-SiR^{21}_2OR^{21}$, $-OSiR^{21}_3$, $-OSi(OR^{21})_3$, $-OSiR^{21}(OR^{21})_2$, $-OSiR^{21}_2OR^{21}$, $-OR^{19}$, $-COR^{19}$, $-CO_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$, or $-N=CR^{19}R^{20}$, where $R^{19}$, $R^{20}$ and $R^{21}$ are each independently selected from H, monovalent substituted or unsubstituted aliphatic and aromatic hydrocarbon radicals having 1 to 25 carbon atoms, but excluding $R^{21}$=H, and M is an alkali metal, alkaline earth metal, ammonium or phosphonium ion. Preferred substituents, especially for X and Y radicals, are tert-butyl and methoxy groups. The $R^1$, $R^2$, $R^3$, $R^4$ radicals are preferably unsubstituted phenyl radicals. Such radicals may, for example, be those as are present in the formulae I-1, I-2 or I-3.

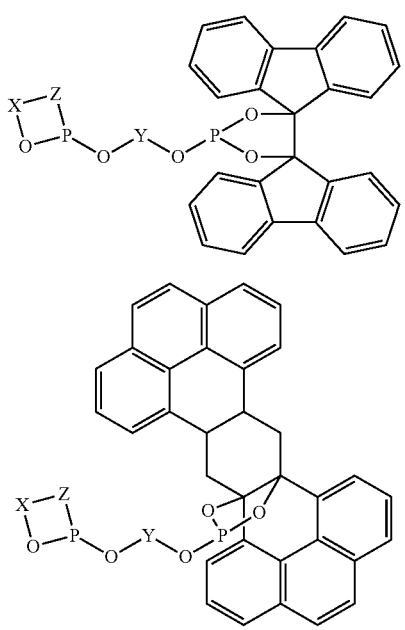

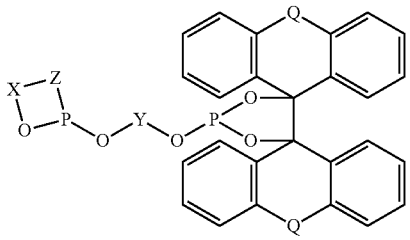

where Q, for example, may be the same or different and may be $CH_2$, $CR^9R^{10}$, $CHR^9$, O, NH or $NR^9$, where $R^9$ and $R^{10}$ may be the same or different and may each be as defined above for $R^9$.

In the bisphosphite, the X radical may also be an Xa radical

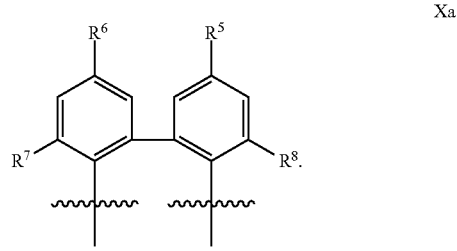

The $R^5$, $R^6$, $R^7$, $R^8$ radicals may each independently be substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms or H, F, Cl, Br, I, $-CF_3$, $-(CH_2)_i(CF_2)_jCF_3$ where i=0-9 and j=0-9, $-SiR^{21}_3$, $-Si(OR^{21})_3$, $-SiR^{21}(OR^{21})_2$, $-SiR^{21}_2OR^{21}$, $-OSi(OR^{21})_3$, $-OSiR^{21}(OR^{21})_2$, $-OSiR^{21}_2OR^{21}$, $-OR^{19}$, $-COR^{19}$, $-CO_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$, or $-N=CR^{19}R^{20}$, where $R^{19}$, $R^{20}$ and $R^{21}$ are each independently selected from H, monovalent substituted or unsubstituted aliphatic and aromatic hydrocarbon radicals having 1 to 25 carbon atoms, but excluding $R^{21}$=H, and M is an alkali metal, alkaline earth metal, ammonium or phosphonium ion.

The $R^5$, $R^6$, $R^7$, $R^8$ radicals may, for example, be substituted by one or more radicals selected from aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms, F, Cl, Br, I, $-CF_3$, $-(CH_2)_i(CF_2)_jCF_3$ where i=0-9 and j=0-9, $-SiR^{21}_3$, $-Si(OR^{21})_3$, $-SiR^{21}(OR^{21})_2$, $-SiR^{21}_2OR^{21}$, $-OSiR^{21}_3$, $-OSi(OR^{21})_3$, $-OSiR^{21}(OR^{21})_2$, $-OSiR^{21}_2OR^{21}$, $-OR^{19}$, $-COR^{19}$, $-CO_2R^{19}$, $-CO_2M$, $-SO_2R^{19}$, $-SOR^{19}$, $-SO_3R^{19}$, $-SO_3M$, $-SO_2NR^{19}R^{20}$, $-NR^{19}R^{20}$, or $-N=CR^{19}R^{20}$, where $R^{19}$, $R^{20}$, $R^{21}$ and M may each be as defined above. In the Xa radical, the $R^5$ to $R^8$ radicals are preferably each hydrogen, alkoxy groups, especially methoxy groups, or tert-butyl groups. Preferably, the $R^5$ and $R^6$ radicals and the $R^7$ and $R^8$ radicals are each identical pairs. More preferably the $R^5$ and $R^6$ radicals are methoxy groups and/or the $R^7$ and $R^8$ radicals are tert-butyl groups.

The X in the bisphosphite is preferably an ethylene radical substituted by $R^{1'}$, $R^{2'}$, $R^{3'}$ and $R^{4'}$ radicals, where the $R^{1'}$, $R^{2'}$, $R^{3'}$ and $R^{4'}$ radicals may be identical or different, substituted or unsubstituted, connected, unconnected or fused aryl or heteroaryl radicals. Possible substituents for the $R^{1'}$ to $R^{4'}$ radials are the substituents specified for the $R^1$ to $R^4$ radicals. Particularly preferred bisphosphites are those which are symmetrical, i.e. those in which X is an ethylene radical substituted by the $R^{1'}$, $R^{2'}$, $R^{3'}$ and $R^{4'}$ radicals, where the $R^1$ and $R^{1'}$, $R^2$ and $R^{2'}$, $R^3$ and $R^{3'}$ and $R^4$ and $R^{4'}$ radicals are each identical.

The divalent Y radical in the inventive bisphosphite may preferably be a substituted or unsubstituted bisphenyl radical or bisnaphthyl radical. Possible substituents may be the abovementioned substituents. The Y radical is preferably selected from the bisphenoxy radicals of the formulae IIa to IId

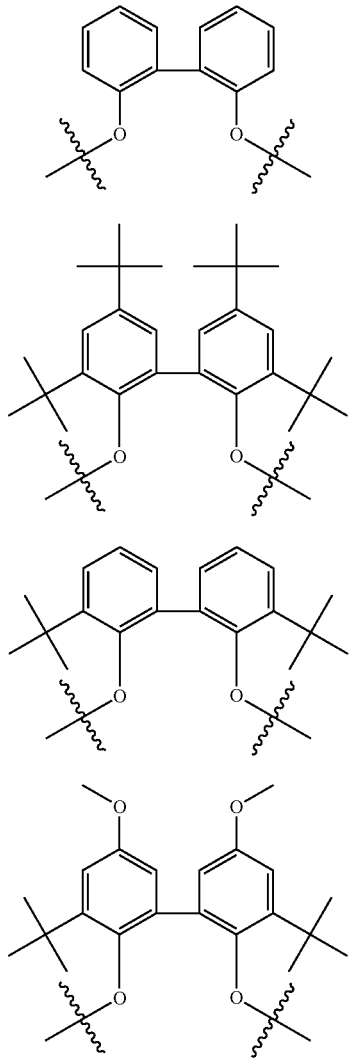

IIa

IIb

IIc

IId or bisnaphthoxy radicals of the formula III

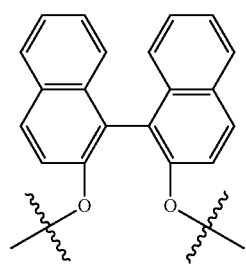

III which may be present in racemic, atropisomerically enriched or atropisomerically pure form.

Particularly preferred inventive bisphosphites are the bisphosphites of the following formulae Ia to Ic, where Ic may be prepared and used as the racemate or in atropisomerically enriched or atropisomerically pure form.

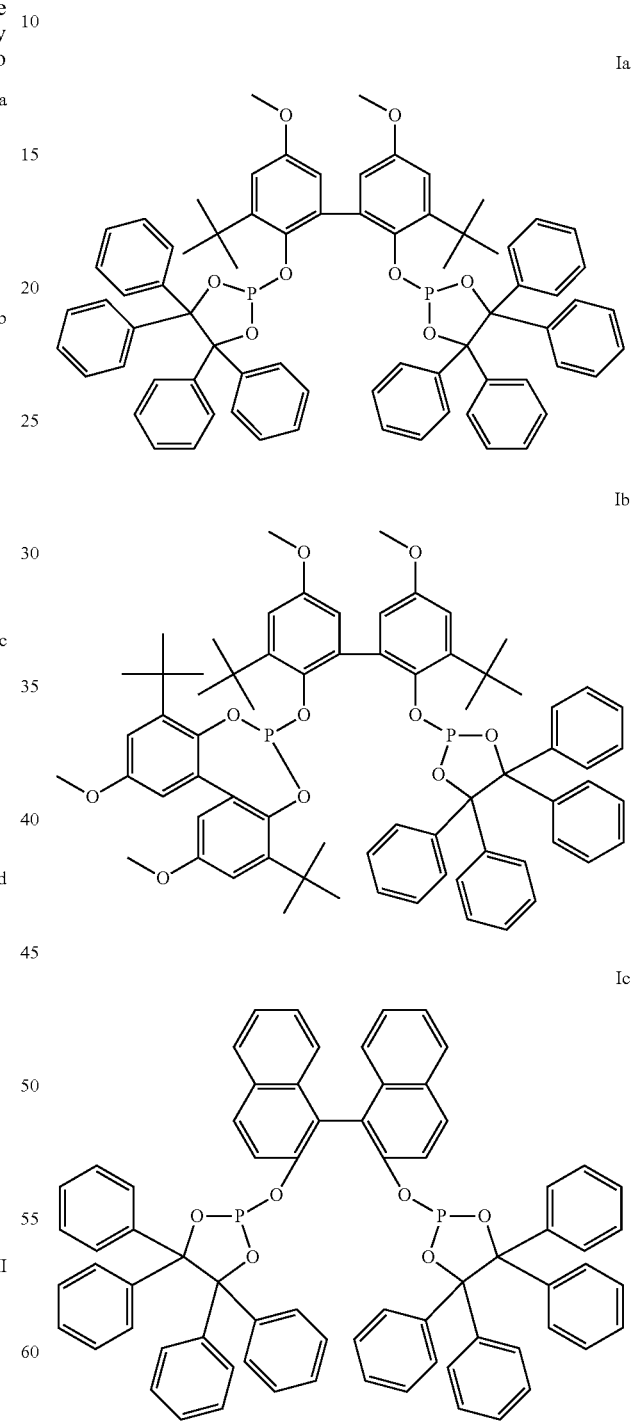

Ia

Ib

Ic

Very particular preference is given to using the catalyst system consisting of rhodium and the bisphosphite with the following structural formula Ia

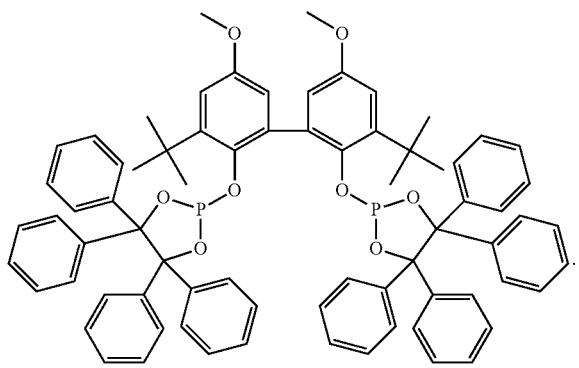

Ia

In the catalyst system, the molar ratio of bisphosphite to rhodium is in the range from less than 100:1 to 1:1, especially in the range from 90:1 to 2:1, very particularly in the range from 10:1 to 2:1.

The rhodium can be used in the form of salts or complexes, for example in the form of rhodium carbonyls, rhodium nitrate, rhodium chloride, $Rh(CO)_2(acac)$ (acac=acetylacetonate), rhodium acetate or rhodium carboxylates or rhodium octanoate.

Bisphosphite ligands and the rhodium compound form, under reaction conditions, the active catalyst species for the homogeneous catalysis. In the course of hydroformylation, on contact of the inventive bisphosphite ligand and of the catalyst metal with synthesis gas, a carbonyl hydride phosphite complex is presumed to be formed as the active catalyst species. The bisphosphites and any further ligands may be added to the reaction mixture in free form together with the catalyst metal (as a salt or complex), in order to generate the active catalyst species in situ. It is additionally also possible to use an inventive phosphite metal complex which contains the abovementioned bisphosphite ligands and the rhodium metal as a precursor for the actually catalytically active complex. These phosphite-metal complexes are prepared by reacting rhodium in the form of a chemical compound or in the 0 oxidation state with the inventive bisphosphite ligand.

Fresh bisphosphite can be added to the reaction at any time, in order, for example, to keep the concentration of free ligand constant.

The concentration of the rhodium in the hydroformylation mixture is preferably 1 ppm by mass to 1000 ppm by mass and preferably 5 ppm by mass to 300 ppm by mass, based on the total weight of the reaction mixture.

The hydroformylation reactions performed with the corresponding rhodium complexes can be performed by known methods, as described, for example, in J. FALBE, "New Syntheses with Carbon Monoxide", Springer Verlag, Berlin, Heidelberg, N.Y., page 95 ff., (1980). In these methods, 1-butene is reacted in the presence of the catalyst with a mixture of CO and $H_2$ (synthesis gas) to give $C_5$ aldehydes.

In this case, the $C_5$ aldehyde fraction contains a proportion of greater than 90% by mass, especially of one of greater than 93% by mass, of n-valeraldehyde, more preferably of greater than 95% by mass and most preferably of greater than 98% by mass of n-valeraldehyde.

The hydroformylation is performed at temperatures of 40 to 120° C., preferably at 40 to 110° C., more preferably at 60 to 95° C., most preferably at 70 to 95° C. The pressure is 0.1 to 30 MPa, especially 1 MPa to 6.4 MPa. The molar ratio between hydrogen and carbon monoxide ($H_2/CO$) in the synthesis gas is preferably 10/1 to 1/10 and more preferably 1/1 to 2/1.

The catalyst system is preferably dissolved homogeneously in the liquid hydroformylation mixture consisting or reactants (olefins and dissolved synthesis gas) and products (aldehydes, alcohols, by-products formed in the process, especially high boilers). Optionally, it is additionally possible to use solvents and/or stabilizer compounds, for example sterically hindered secondary amines or promoters.

The process can be performed batchwise or preferably continuously. In a continuous process, it is appropriate, in order to achieve virtually complete 1-butene conversion, to perform the reaction in a plurality of reactors. For example, it is possible to connect a plurality of stirred reactors and/or bubble column reactors in series. In this case, the liquid and/or gaseous effluent of a reactor can be passed into the next. It is also possible to draw off unconverted feed hydrocarbons from a reactor together with products and excess synthesis gas, to condense out the $C_5$ products, and to introduce the residual gas into the next reactor. The reaction can also be carried out in a pipe coil with intermediate gas feeding. In addition, the reactor can be carried out in a combination of the reactor types mentioned.

If the aim is not the maximum yield of $C_5$ aldehydes but a high space-time yield, the hydroformylation can be conducted at least partly at temperatures of more than 100° C. At these temperatures, partial isomerization of 1-butene to the two 2-butenes occurs during the hydroformylation. For example, it would be possible to operate the first reactor or the first reactors in a reactor cascade at temperatures of more than 100° C. and the downstream reactor(s) at temperatures of less than 100° C., for example 90° C.

The hydroformylation product can be separated by distillation into at least three fractions, specifically into the isobutene fraction, product fraction (principally $C_5$ aldehydes) and a high boiler fraction comprising the dissolved catalyst system and one or two further fraction(s) which comprise(s) other unconverted substances from the reactant.

For example, the reaction mixture of the last reactor, after removal of the excess synthesis gas, which can be recycled or discharged completely or partially after condensing out substances present therein, can be separated by a first distillation into a $C_4$ hydrocarbon mixture and a mixture of $C_5$ products, high boilers and catalyst system. The two mixtures are separated in further distillation steps.

Another possibility is to remove fractions one by one from the reaction mixture, beginning with the lowest-boiling substance or substance mixtures, until only the high boilers comprising the dissolved catalyst system remain.

Optionally the distillative removal can be preceded by removal of a portion of the catalyst by nanofiltration, as described, for example, in DE 10 2005 046250.

If, for example, the reactant used was a $C_4$ hydrocarbon mixture which comprised isobutane, n-butane, 1-butene, the two 2-butenes and isobutene, the following fractions are obtained:

a) isobutane (boiling point −11.7° C.)
b) isobutene (b.p.−6.9° C.)
c) mixture of n-butane (b.p. −0.5° C.), E-2-butene (b.p. 0.9° C.) and Z-2-butene (b.p. 3.7° C.)
d) mixture of $C_5$ aldehydes with valeraldehyde (b.p. 103° C.), 2-methylbutanal (b.p. 92-93° C.) and 3-methylbutanal (b.p. 92.5° C.)
e) high boilers comprising the dissolved catalyst system Isobutene removed by the process according to the invention has a purity of more than 99%. Its content of linear butenes is correspondingly below 1%. It can be utilized for the purposes mentioned in the introduction.

The $C_5$ aldehyde fraction contains small amounts of alcohols which arise through hydrogenation of the aldehydes. The content of valeraldehyde in this fraction is more than 95% by mass. Pure valeraldehyde can be removed from this mixture. Valeraldehyde is, among other things, an intermediate for n-pentanol, n-pentanoic acid, n-pentylamines or n-pentyl chloride.

Aldol condensation of the $C_5$ aldehyde fraction and total hydrogenation of the aldol condensate affords a decanol mixture containing more than 90% by mass of 2-propylheptanol, which is a sought-after intermediate for the production of plasticizers, detergents and lubricants. Aldol condensation of the $C_5$ aldehyde fraction, hydrogenation of the olefinic double bond of the aldol condensate and subsequent oxidation of the aldehydic group can provide a decanoic acid mixture with a high proportion of 2-propylheptanoic acid, which can be used, for example, to produce lubricants or detergents.

The fraction comprising the 2-butenes can be utilized in different ways. One possibility is the preparation of oligomers, among which especially the dimers and trimers constitute valuable intermediates for the production of plasticizers and alcohols. The oligomerization can be carried out using acidic or nickel-containing catalysts. When low-branching products are desired, an oligomerization with a nickel-containing, heterogeneous catalyst system is advantageous. One process of this kind is, for example, the OCTOL process of Evonik Oxeno GmbH.

Another utilization of the 2-butenes consists in hydroformylating them to $C_5$ aldehydes. The hydroformylation can be carried out with different catalysts, and typically forms a mixture of 2-methylbutanal and n-valeraldehyde. When a high proportion of valeraldehyde in the $C_5$ aldehyde mixture is desired, the use of other catalysts is appropriate. For example, in documents DE 101 08 474, DE 101 08 475, DE 101 08 476 and DE 102 25 282, a catalyst consisting of rhodium and a diphosphine ligand which has a xanthene skeleton is used for the hydroformylation of 2-butenes. Using this catalyst, the ratio between valeraldehyde and 2-methylbutanal is greater than 85:15. High selectivities of valeraldehyde (greater than 95%) can be obtained in the case of use of a catalyst consisting of rhodium and sterically demanding aromatic bisphosphites, as described, for example, in EP 0 213 639.

The $C_5$ aldehyde mixture thus obtained can be converted, for example by aldol condensation and subsequent hydrogenation of the aldol condensate, to a decanol mixture. In the case of $C_5$ aldehyde mixtures in which the proportion of n-valeraldehyde is less than 95%, it is advisable to remove a proportion of the 2-methylbutanal by distillation in order to obtain a high-quality decanol mixture with a content of 2-propylheptanol of more than 90%.

The 2-methylbutanal removed can be used for various purposes, for example for preparing isoprene.

When the preparation of decanol from a $C_4$ hydrocarbon mixture is the aim, it is appropriate to aldolize the $C_5$ aldehyde mixtures of the two hydroformylations together.

EXAMPLES

The hydroformylation test was carried out in a Parr 100 ml autoclave with means of keeping the pressure constant, gas flow meter and paddle stirrer. The autoclave was filled under an argon atmosphere with all compounds specified below, but not yet with the olefin mixture to be hydroformylated. After exchanging the argon atmosphere by purging with synthesis gas (1:1 $CO/H_2$), the reaction mixture was heated with stirring (1000 rpm) and under synthesis gas pressure to the temperature specified in each case, and then the exact target pressure of 20 bar was established. Subsequently, the olefin mixture to be hydroformylated was added. The synthesis gas pressure was kept constant by means of a pressure regulator over the entire reaction time. The reaction time of the hydroformylation tests was in each case 720 min, intermediate samples having been taken from the autoclave for GC analysis. Subsequently, the reaction mixture was cooled to room temperature, and the autoclave was decompressed and purged with argon.

All tests contained 6 g of the olefin mixture to be hydroformylated (raffinate I of the composition specified below), 50 g of eutectic mixture of biphenyl and biphenyl ether (Diphyl®, from Lanxess) and bis(2,2,6,6-tetramethyl-4-piperidyl)sebacate (from Ciba) in a molar ratio of 1:1 relative to the ligand Ia used. The precatalyst used was (acetylacetonato) dicarbonylrhodium (from Umicore).

Tests were carried out at 90° C., 100° C., 110° C. and 120° C. The ratio of ligand Ia to rhodium was in all cases 5:1, the rhodium concentration was 40 ppm and the synthesis gas pressure was 2 MPa.

The analysis was carried out by means of gas chromatography.

The raffinate I had in each case the start composition specified in Table 1 (all values in % by mass):

TABLE 1

| Component | Iso-butane | n-Butane | E-2-Butene | 1-Butene | Iso-butene | Z-2-Butene | 1,3-Butadiene | Remainder |
|---|---|---|---|---|---|---|---|---|
| in % by mass | 4.09 | 10.63 | 7.69 | 26.81 | 45.72 | 4.68 | 0.18 | 0.20 |

Example

Hydroformylation of Raffinate I at Different Temperatures

The hydroformylation of raffinate I of the above composition was carried out at 90° C., 100° C., 110° C. and 120° C. In all cases, no 1-butene could be detected any longer after 720 minutes, which showed quantitative conversion of the 1-butene. At the same time, the particular isobutene conversion (formation of 3-methylbutanal) after 720 minutes was at the following values:
90° C.: 0.58%
100° C.: 0.67%
110° C.: 0.80%
120° C.: 1.17%

The hydrogenation to saturated species likewise played only a minor role and was less than one percent, and less than one-and-a-half percent at temperatures from 110° C.

In the tests at 110° C. and 120° C., there was also a certain degree of isomerising hydroformylation of the 2-butenes toward the end of the reaction, such that the yield of n-valeraldehyde in these cases after 720 minutes was 102% and 105% respectively, based on 1-butene used in the raffinate I.

The pentanal formed from 1-butene (and, from 110° C., to a minor degree from 2-butenes) after 720 minutes was obtained with the following linearities:
90° C.: 99.1%
100° C.: 99.0%
110° C.: 98.9%
120° C.: 98.4%

The differences from 100% are 2-methylbutanal.

The invention claimed is:

1. A process for removing 1-butene from a $C_4$ hydrocarbon mixture comprising isobutene and 1-butene by hydroformylation, said process comprising
hydroformulating a hydroformulation mixture comprising said $C_4$ hydrocarbon mixture and a catalyst system comprising one or more of the transition metals of groups 8 to 10, and a bisphosphite ligand of the following formula I

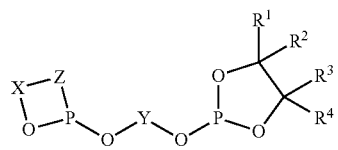

where X is a divalent substituted or unsubstituted bisalkylene or bisarylene radical which comprises one or more heteroatom(s), Y is a divalent substituted or unsubstituted bisarylene radical or a divalent substituted or unsubstituted bisalkylene radical which comprises one or more heteroatom(s), Z is oxygen or $NR^9$, and $R^1$, $R^2$, $R^3$, $R^4$ are identical or different, substituted or unsubstituted, connected, unconnected or fused aryl or heteroaryl radicals, and $R^9$ is hydrogen or substituted or unsubstituted alkyl or aryl radical which comprises one or more heteroatom(s), the bisphosphite ligand of the above-specified formula I being in an excess of a molar ratio of 100:1 to 1:1 relative to the transition metal, and less than 5% of the isobutene present being converted at a 1-butene conversion of more than 95%.

2. The process according to claim 1, wherein the concentration of the transition metal in the hydroformylation mixture is 1 ppm by mass up to 1000 ppm by mass based on the total weight of the reaction mixture.

3. The process according to claim 1, wherein the transition metal is rhodium and the molar ratio of bisphosphite to rhodium is in the range from 90:1 to 1:1.

4. The process according to claim 1, wherein the transition metal is rhodium and the molar ratio of bisphosphite to rhodium is in the range from 10:1 to 2:1.

5. The process according to claim 1, wherein less than 5% of the isobutene present is converted at a 1-butene conversion of more than 99%.

6. The process according to claim 1, wherein 1-butene is hydroformylated with an n-/iso selectivity of more than 97%.

7. The process according to claim 1, wherein 1-butene in the feed hydrocarbon mixture is removed to an extent of more than 99% from the $C_4$ hydrocarbon mixture by hydroformylation at a temperature of from 40 to 120° C.

8. The process according to claim 1, wherein 1-butene in the feed hydrocarbon mixture is removed to an extent of more than 99% from the $C_4$ hydrocarbon mixture by hydroformylation at a temperature of from 70 to 95° C.

9. The process according to claim 1, wherein the hydroformylation is carried out within a pressure range of from 0.5 to 30 MPa.

10. The process according to claim 1, wherein the hydroformylation is carried out within a pressure range of from 1.0 to 6.4 MPa.

11. The process according to claim 1, wherein the process is performed continuously.

12. The process according to claim 1, wherein the $C_4$ hydrocarbon mixture comprises 2-butene.

13. The process according to claim 1, wherein the reaction mixture is separated into $C_5$ aldehyde, isobutene, a high boiler fraction comprising the dissolved catalyst system and $C_4$ hydrocarbon.

14. The process according to claim 13, wherein the further $C_4$ hydrocarbon is subjected to an isomerizing hydroformylation to give valeraldehyde.

15. The process according to claim 14, wherein the $C_5$ aldehydes obtained from selective hydroformylation and isomerizing hydroformylation are combined.

16. The process according to claim 13, wherein the $C_5$ aldehyde removed is subjected to an aldol condensation, dehydration and subsequent hydrogenation to form 2-propylheptanol.

17. The process of claim 1, wherein the catalyst system comprises rhodium.

18. The process of claim 1, wherein the bisphosphite ligand is selected from the group consisting of the following formulae Ia, Ib and Ic:

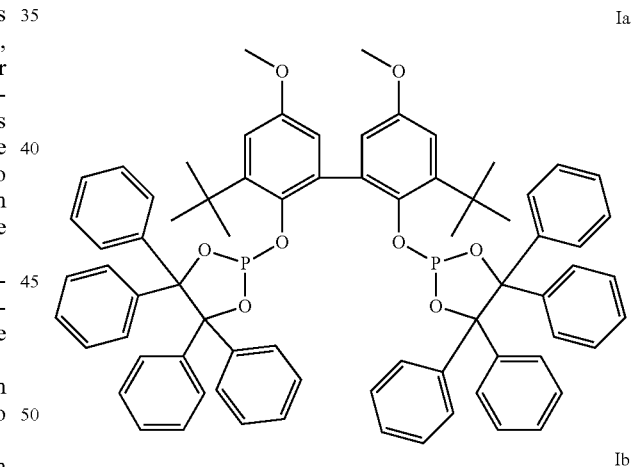

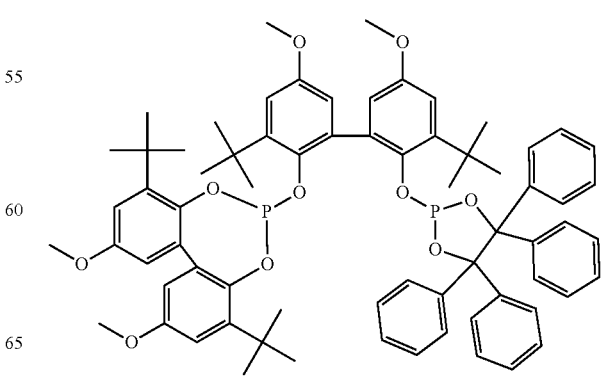

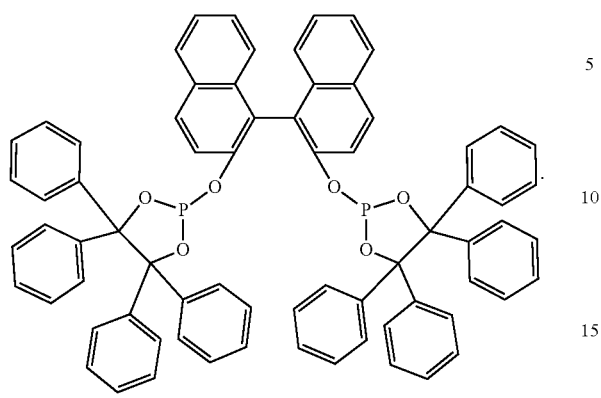
Ic
19. The process of claim 18, wherein the bisphosphite ligand has formula Ia, and the transition metal is rhodium.
* * * * *